(12) United States Patent
Bådenlid et al.

(10) Patent No.: US 7,153,391 B2
(45) Date of Patent: Dec. 26, 2006

(54) METHOD IN CONNECTION WITH THE PRODUCTION OF PULP, PAPER OR PAPERBOARD

(75) Inventors: Raija Bådenlid, Karlstad (SE); Staffan Andersson, Brastad (SE); Eva-Lena Strömberg, Brastad (SE); Jenny Bergström, Karlstad (SE)

(73) Assignee: Stora Enso Aktiebolag, Falun (SE)

( * ) Notice: Subject to any disclaimer, the term of this patent is extended or adjusted under 35 U.S.C. 154(b) by 401 days.

(21) Appl. No.: 10/257,538

(22) PCT Filed: Apr. 5, 2001

(86) PCT No.: PCT/SE01/00740

§ 371 (c)(1),
(2), (4) Date: Dec. 23, 2002

(87) PCT Pub. No.: WO01/79816

PCT Pub. Date: Oct. 25, 2001

(65) Prior Publication Data

US 2003/0155092 A1 Aug. 21, 2003

(30) Foreign Application Priority Data

Apr. 14, 2000 (SE) .................................. 0001419

(51) Int. Cl.
*D21F 13/00* (2006.01)
(52) U.S. Cl. ................. 162/198; 162/49; 162/DIG. 10; 702/29; 702/30; 702/33; 250/339.12; 250/343
(58) Field of Classification Search .................. 162/49, 162/198, DIG. 10; 702/32, 29–30, 33; 250/339.12, 250/334.07, 343
See application file for complete search history.

(56) References Cited

U.S. PATENT DOCUMENTS 5,680,321 A * 10/1997 Helmer et al. ................. 702/30

FOREIGN PATENT DOCUMENTS

| WO | WO 95/31710 A1 | 11/1995 |
| WO | WO 98/28486 A1 | 7/1998 |

* cited by examiner

*Primary Examiner*—Mark Halpern
(74) *Attorney, Agent, or Firm*—Nixon & Vanderhye (57) ABSTRACT

Method for predicting properties of a product of cellulose-fibre-based pulp, paper or paperboard, wherein a suspension of cellulose fibre is subjected to analysis, during manufacture of the product, by spectroscopic measurements of a sample quantity of the suspension, in a spectrum in the wavelength range 200–2500 nm. The method comprises diluting each sample quantity prior to analysis, dewatering and drying one partial flow and subjecting that partial flow to spectroscopic measurements, and analyzing a second partial flow of the diluted sample quantity for physical fiber data, by means of image analysis. Each sample quantity analyzed generates at least 100 data points from the spectroscopic measurement distributed in the selected spectrum, and at least 50 data points with regard to the physical fibre data, in the form of one or more physical fibre property distributions with regard to at least one physical property selected from fibre length, fibre width and fibre shape. The data points are combined in multivariate data processing for prediction of properties of the product, on the basis of calibrations previously executed on samples with known properties.

21 Claims, 9 Drawing Sheets

METHOD IN CONNECTION WITH THE PRODUCTION OF PULP, PAPER OR PAPERBOARD

This application is the U.S. National Phase of International Application PCT/SE01/00740, filed 5 Apr. 2001, which designated the U.S. PCT/SE01/00740 claims priority to Swedish Application No. 00014191 filed 14 Apr. 2000. The entire content of these applications are incorporated herein by reference.

TECHNICAL FIELD

The present invention relates to a method for predicting the properties of a product that consists of cellulose-fibre-based pulp, paper or paperboard, a suspension of cellulose fibre being analysed during manufacture of the product by means of spectroscopic measurements of a sample quantity of said suspension in a selected spectrum in the wavelength range 200–25000 nm. According to the invention, physical fibre data are also analysed for the suspension. Multivariate methods are used to analyse the combination of measuring data obtained. The invention can be applied to both chemical and mechanical pulps.

PRIOR ART

The commercial production of paper and paperboard often takes place in at least two mill units separated from one another, the paper pulp producer manufacturing the paper pulp in a first mill and delivering the same in a dried state to the paper or paperboard manufacturer, who produces the paper or paperboard in a second mill. Even in integrated mills, i.e. mills where both pulp and paper or paperboard are produced, the division between the two different parts is clear both as regards the position of the physical installations and their operation. The properties of the pulp produced can thus be said to constitute a "half-time" result, representing the control objective for the pulp producer and the starting point for the paper or paperboard manufacturer.

Producers of paper pulp are confronted today with very high demands for the pulp that they supply to be of a high, consistent and well-documented quality. Since the raw material for the pulp produced varies depending on the type of tree, its locality, the age of the tree, the storage time, the proportion of summer wood/spring wood and the proportion of round timber/sawmill chips, the properties of the pulp will vary with a starting point in these variations. The properties of the pulp are also influenced by variations in the manufacturing process, e.g. varying chip quality, cooking conditions, washing results, changes in the bleaching stages, variations in presses and mixers, and other planned or unplanned production changes.

To be able to offer the customers, i.e. the paper and paperboard manufacturers, pulp that precisely matches their requirements specifications, which specifications differ between different paper or paperboard manufacturers depending on the product that they manufacture, it is necessary to be able to measure and predict the properties that reflect the product quality that the respective customer wishes to produce. Starting out from measured or predicted properties of this kind, it should be possible to direct each individual base paper bale or roll produced to precisely the customer to which it is suited. To achieve this, it is of the highest importance to be able to generate relevant measuring data that is highly reliable. Since pulp production is continuous, it is also desirable for measuring data to be generated continuously. The continuous generation of measuring data should also offer the opportunity of seeing the effect of changes in the raw material and process and of thereby steering the process towards the desired pulp quality.

Furthermore, it is desirable for the pulp producer to be able to specify at the time that he delivers the pulp how this pulp in particular should be beaten for the desired product attributes to be achieved. For the pulp producer, it would therefore be extremely valuable to have an analysis tool that shows the potential of a given pulp, depending on how it is beaten in a subsequent stage, i.e. depending on the energy input that is used in subsequent beating.

The methods used commercially today for classifying the pulp produced are not adequate either with regard to continuity or reliability. Nor is it possible to relate the measured attributes of the pulp to the attributes of the paper or paperboard produced, depending on how the pulp is beaten. The quality of the finished pulp is judged today by measuring parameters such as brightness, purity and viscosity with a certain regularity on a selection of production. Customer specifications based on the parameters that describe the strength of the pulp are only measured as random samples, since these analyses are both staff-intensive and time-consuming. The possibility of recording changes between different process stages is often limited to measurements of the kappa number and viscosity. A problem is also constituted by the fact that the properties of the pulp produced vary over a 24-hour period, as has been shown, and that the parameters that are measured most frequently, viscosity, purity and brightness, more often than not are not relevant measurements of the strength of the pulp.

In a number of articles from 1989 onwards, it has been shown that spectroscopy in the near infrared range (NIR) can be used, separately or together with multivariate analysis (MVA), to determine the chemical and physical parameters of paper pulp:

Birkett, M. D. and Gambino M. J. T., *Estimation of pulp kappa number with near-infrared spectroscopy*, Tappi J. September 193–197, (1989);

Easty D. B., et al., *Near-infrared spectroscopy for the analysis of wood pulp: quantifying hardwood-softwood mixtures and estimating lignin content*, Tappi J. 73 (10), 257–261, (1990);

Wallbäcks, L., Edlund, U and Norden, B., *Multivariate characterization of pulp, part 1, Spectroscopic characterization of physical and chemical differences between pulps using 13C CP/MAS NMR, FT-IR, NIR and multivariate data analysis*, Nordic Pulp and Paper Research Journal no. 2, 74–80, (1991);

Wallbäcks, L., Edlund, U and Norden, B., *Multivariate characterization of pulp, part 2, Interpretation and prediction of beating processes*, Nordic Pulp and Paper Research Journal no. 3, 104–109, (1991);

Wallbäcks, L., *Characterization of chemical pulps using spectroscopy, fibre dimensions and multivariate data analysis*, Proceedings 7$^{th}$ international symposium on wood and pulping chemistry, 802–809, (1993);

Wallbäcks, L., Edlund, U and Lindgren, T. *Multivariate characterization of pulp, part 3, Evaluation of physical and spectroscopic data on unbeaten and beaten kraft pulp samples*, Nordic Pulp and Paper Research Journal no. 2, 88–93, (1995);

Olsson, R. J. O., Tomani P., Karlsson M., Josefsson T., Sjöberg K. and Björklund C.: *Multivariate characterization of chemical and physical descriptors in pulp using NIRR*, Tappi J., Vol. 78, No. 10 (1995);

Antti, H and Sjöström, M., *Multivariate calibration models using NIR spectroscopy on pulp and paper industrial applications,* Journal of Chemometrics, Vol. 10, 591–603, (1996);

Marklund, A., et al., *Prediction of strength parameters for softwood kraft pulps. Multivariate data analysis based on orthogonal signal correction and near infrared spectroscopy,* Nordic Pulp and Paper Research Journal Vol. 14 no. 2, 140–148 (1999);

Liljenberg, T., et al., *On-line NIR characterization of pulp,* 10th International Symposium on Wood and Pulping Chemistry, 266–269 (1999).

It is also known that physical fibre properties, which are measured using different types of fibre meters, are of great significance for the strength attributes of the pulp. The possibility of using several length classes and processing these using MVA has been demonstrated by Marklund, A., et al., *Prediction of strength parameters for softwood kraft pulps. Multivariate data analysis based on physical and morphological parameters,* Nordic Pulp and Paper Research Journal Vol. 13 no. 3, 211–219 (1998).

There are also some patent applications that relate to the field of NIR linked to paper pulp; WO 93/05384, WO 95/31710 and WO 95/31709. However, none of these link together the use of NIR data and physical fibre data with MVA. In other cases, according to the aforementioned references, where it is indicated that fibre data such as fibre length can be used together with NIR data, the form in which the fibre data is used is not specified.

It is in this regard traditionally the case that only mean values or rough classifications, and not entire distributions as regards fibre data, have been able to be analysed on-line or at-line.

In WO97/38305, WO98/28486, WO98/28487, WO98/28488 and WO98/28490, Siemens AG described the control and optimization of a process for the manufacture of paper pulp or paper starting out from multivariate analysis of input data in the form of spectra of electromagnetic radiation and/or mechanical properties. In the applications, the use of mechanical properties of the fibres is exemplified by a diagram that shows a distribution curve in which the fibres have been divided up into twelve different fibre length classes, i.e. a relatively rough classification.

In a diploma paper, Bergström M., *Multivariate characterization of mill beaten pulps, using NIR, PQM 1000 and FiberMaster,* 1999, Umeå University, the possibility was discussed of combining NIR data and fibre distribution curves with multivariate analysis in order to be able to predict better the properties of the product. In this case, however, the measurements were carried out on beaten pulp and only so-called NIR score vectors were used as input data, i.e. not entire NIR spectra.

ACCOUNT OF THE INVENTION

The object of the present invention is to present a method of predicting the properties of a product which consists of cellulose-fibre-based pulp, paper or paperboard. The method according to the invention is a further development of the above-named techniques and gives relevant prediction results with a very high level of reliability, thanks to the fact that a very large number of data points from both spectroscopic measurements and physical fibre analyses (fibre distributions) is used in combination with multivariate analysis. Furthermore, the measurements are carried out continuously, at-line or on-line, at intervals that permit each base paper bale or roll produced to be characterized individually. This gives a unique opportunity to direct the individual bales or rolls to a customer to whom they are suited.

These and other objects are achieved by means of the method according to the invention, as presented in claim 1.

In a specially preferred embodiment of the invention, a sample quantity is extracted on-line at close intervals in time, at a position in the process line for pulp production that is disposed in advance of beating of the pulp. The sample quantity is preferably extracted directly prior to a drying stage for the pulp, which drying stage is disposed directly prior to sale of the dried pulp or directly preceding beating of the pulp. The analyses according to the invention are thus carried out preferably on the unbeaten pulp. However, a calibration model is created for prediction that comprises calibrations against pulp samples that have been beaten with a number of different energy inputs. A possibility is thus obtained by means of the method according to the invention of predicting potential product properties for a given pulp, depending on how this is beaten in a subsequent stage. The product properties predicted for an individual base paper bale or roll produced in pulp manufacture can thereby be compared with the desired product properties for a number of different paper- or paperboard-manufacturing customers, it being possible to take this comparison as a basis for the choice of customer to whom the bale or roll is delivered. From the predicted properties of the pulp the customer can then advantageously choose how the continued beating strategy shall appear for the desired product attributes to be achieved.

According to one aspect of the invention, the spectrum within which the NIR measurements are carried out consists of the wavelength range 400–2500 nm, preferably 780–2500 nm. Within this spectrum, at least 100 data points, preferably at least 300 data points, even more preferredly at least 500 data points and most preferredly at least 800 data points are generated by means of transmission or reflectance for each sample quantity extracted.

These data points also preferably consist of mean values from a number of sweeps in the spectrum, preferably at least 10 sweeps.

According to another aspect of the invention, said physical fibre data is obtained by means of CCD camera and image analysis, preferably by means of an apparatus called the STFI FiberMaster, around 10000 fibre images being analysed for each sample quantity and put together to form at least 50 data points, preferably at least 100 data points and even more preferredly at least 150 data points. These data points consist according to the invention of distribution data and mean values with regard to at least one, preferably at least two and even more preferredly all physical properties in the group that consists of fibre length, fibre width and fibre shape, and preferably also of fibre weight per metre and fibre flexibility.

One problem in connection with combined at-line or on-line fibre analysis and NIR is that the fibre analysis takes a relatively long time, since up to 10000 individual fibres are to be photographed for each sample. This also means that the sample has to be very diluted for the individual fibres to be visible. For NIR, on the other hand, it is the case that the analysis is very quick, but that the sample should have a relatively high dry content, often at least 50% depending on the measuring position. According to one aspect of the invention, these apparently incompatible requirements are satisfied by a sample quantity extracted being diluted while being agitated to a concentration of less than 0.5%, preferably less than 0.1%. A partial flow of the sample quantity is then used for analysing the physical fibre data, and another partial flow is dewatered and dried to at least 50% dry content, preferably at least 70% dry content, and used for the spectroscopic measurements. The dewatering and drying is best carried out by filtering combined with forced air drying, preferably by means of direct contact with compressed air. The drying takes a little time, but the two analyses will nevertheless be in phase, since the fibre analysis also takes some time.

According to one aspect of the invention, the multivariate analysis is carried out using Principal Component Analysis (PCA), Principal Component Regression (PCR), Partial Least Squares Regression (PLS) or Multiple Linear Regression (MLR). The principle of multivariate analysis (NVA) utilizing PCA is that a multidimensional data quantity with variables correlating to one another is projected to a smaller data quantity with non-correlating variables containing relevant information at the same time as back noise is eliminated. In general, 2–10 principal components can account for 98% of the variance in the data quantity. PLS is a regression method which uses the information from y-data in a principal component distribution of x-data and relates this to the property y sought. PLS or one of the other methods named above is used to set up the calibration model.

The properties that are predicted according to the invention can be one or more of the properties that are included in the group dewatering resistance, density, tensile index, rupture working index, burst index, tear index, tensile rigidity index, surface coarseness, beating requirement, opacity, toughness, light scattering, zero span, air permeance, air resistance, carbohydrate composition, charged groups, fibre type distribution, kappa number, lignin, hexenuronic acid, gravity, brightness, moisture content, viscosity, runnability or other. To determine the calibration model, these properties are thus analysed using traditional laboratory analysis for a number of samples, following which calibration is carried out between these laboratory results and the results of the multivariate analysis, so that a calibration model is obtained that is used for predicting the above-named properties in future at-line or on-line measurements. The calibration model is used to estimate the parameters which are regarded as relevant for the respective customer. In calibration, a distribution of samples is sought that is representative of the process and thereby covers the variation that can be found in the pulp. The calibration model is verified using an internal validation model (cross-validation), which gives a measure of the model's reliability, e.g. by means of a so-called Q2 value, and samples analysed using an independent set (external validation), a measure being obtained of how well the model functions in practice.

The principle of how MVA is carried out is well known, e.g. from the aforementioned references that describe the prior art, and will not therefore be described in greater detail here. For optimum prediction with the use of MVA, some supplementary data processing can be carried out, for example weighting of variables and/or processing of spectral raw data using Orthogonal Signal Correction (OSC), Multiplicative Scatter Correction (MSC), Standard Normal Variate transformation (SNV) or by using a derivator.

BRIEF DESCRIPTION OF DRAWING

The application of the method according to the invention in the mill will be described below and examples will be given with reference to the figures, of which.

Figure 1:
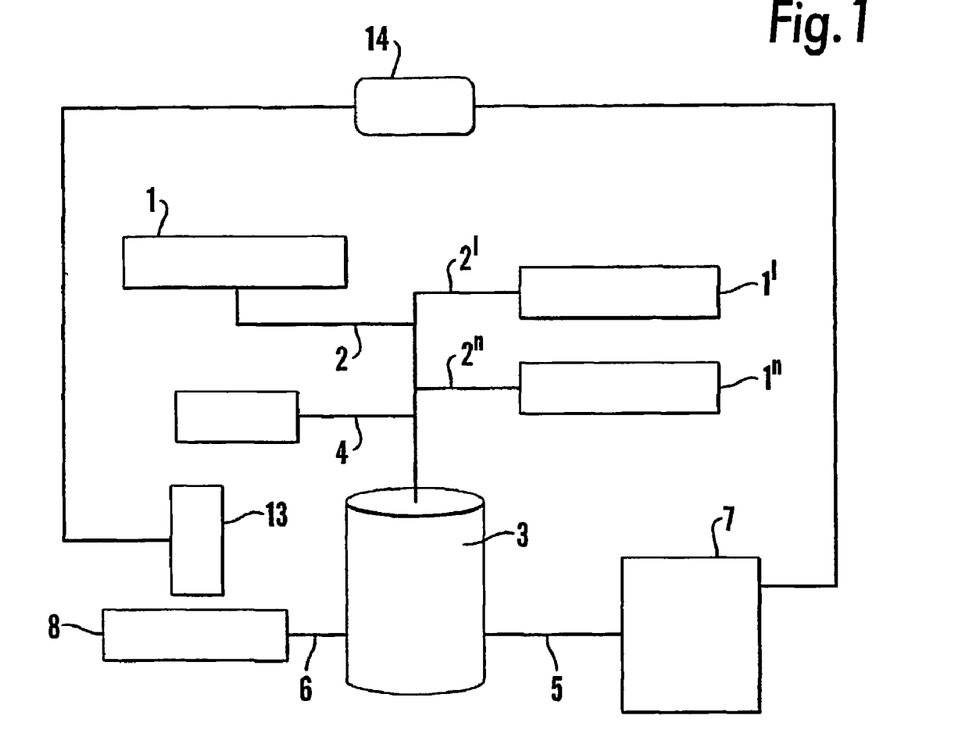
FIG. 1 shows an elementary diagram of a preferred apparatus set-up for sampling on-line in a pulp mill.

In a pulp mill, e.g. a mill for manufacturing bleached chemical pulp, a sample quantity is extracted on-line, i.e. a sample flow is extracted by one or more sampling devices 1, 1', 1" and taken away from the production line via lines 2, 2', 2" to be analysed in parallel with the same (FIG. 1). Sampling takes place continuously, at least once every two hours, preferably at least once per hour, even more preferredly at least twice per hour and most preferredly of all at least four times per hour. In certain cases, however, it is conceivable for sampling to take place at longer intervals. The position for sampling can be anywhere in the pulp line, preferably at the end of the pulp line, prior to beating. Moreover, beating does not normally take place in the pulp line, but in the subsequent line for paper or paperboard production.

The sample quantity extracted is pumped through the lines 2, 2', 2" down into a vessel 3 for dilution of the same. Water is added via the line 4 during simultaneous agitation of the vessel 3, so that the sample in the vessel attains a concentration of a few hundredths of a percent. The sample is then divided into a first partial flow 5 and a second partial flow 6. The first partial flow 5, which can be less than the second partial flow 6, is taken away to equipment 7 for fibre analysis using a CCD camera in a fibre meter, including computer 14. The second partial flow 6 is taken to a dewatering vessel 8 for dewatering and drying.

Figure 2:
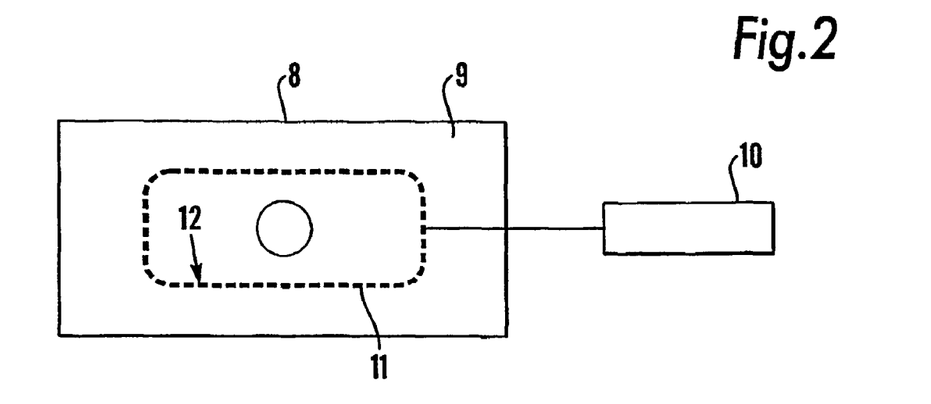
FIG. 2 shows a dewatering vessel in the apparatus set-up according to FIG. 1, seen from above.

FIG. 2 shows the dewatering vessel 8, seen from above. The dewatering vessel 8 consists of an open box with a filter 9 arranged in its lower part. An outlet (not shown) for the filtrate is arranged under the filter 9, which outlet is preferably connected via a vessel (not shown) to a vacuum pump (not shown) preferably controlled by compressed air. Thanks to the filter and vacuum pump, the sample attains a dry content of around 20%. To attain the desired dry contents for the NIR analysis, a forced drying stage takes place, which preferably utilizes compressed air 10. A ring line 11 is provided here for compressed air, above the filter 9. The ring line 11 has a quantity of outlet openings 12 around the same, which are directed inwards and downwards towards the centre of the vessel 8. When compressed air is blown out through these outlet openings 12, the pulp cake on the filter 9 will be dried to a dry content exceeding 50%. It is perceived that the dewatering vessel 8, even if shown in the figure as a square box, can equally consist of a vessel with a round cross-section, e.g. a cylindrical vessel, the ring line also best following a circular shape.

When drying has been completed, a measuring head 13 for NIR is lowered down towards the filter cake and the NIR measurements are carried out in the spectrum selected. In the example shown, the measurements are performed with reflectance using an instrument that measures in the wavelength range 1100–2300 nm and collects the data in a computer 14, which computer also carries out the MVA analysis. The result of the MVA analysis is then used, and also that in the computer, for predicting the expected attributes of paper or paperboard manufactured from the pulp, from the calibration model set up earlier, with different energy inputs for beating.

Figure 3:
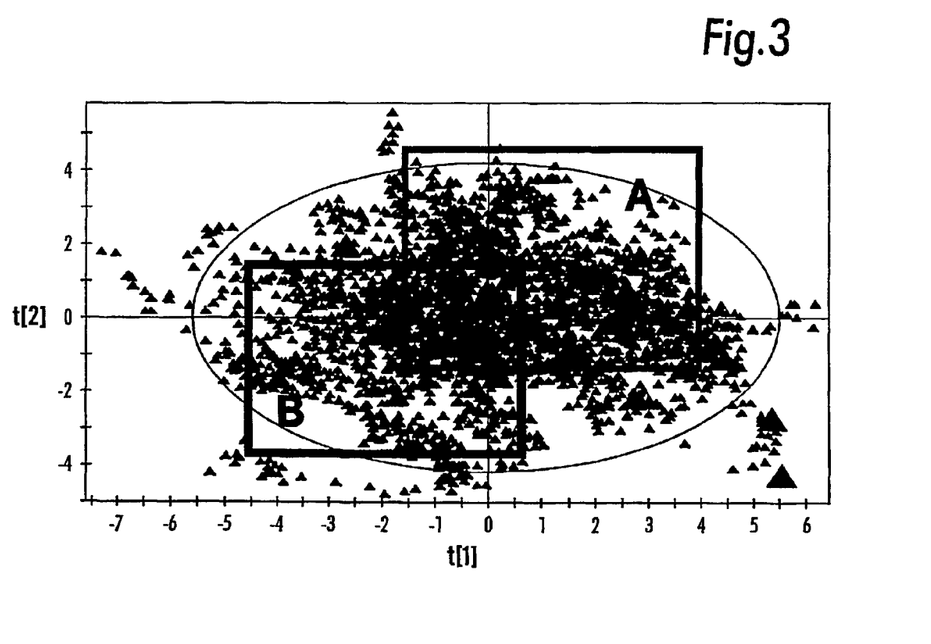
FIG. 3 shows an example of a so-called Score plot.

As an example of the invention, FIG. 3 shows an image in which the results of a large number of continuous measurements have been collected in a so-called score plot, where each point describes a sample. Since the position describes a certain type of properties, a direct classification of the pulp analysed is obtained. The pulp which ends up in the square furthest to the right has an attribute profile that is suited to customer A, while the pulp in the square down to the left meets the requirements set for the pulp for customer B.

EXAMPLE

Elaboration of Calibration Model—Example from Off-Line Study

NIR spectroscopy and fibre analysis are used together with multivariate data analysis (PLS) to determine the tensile index and beating requirement of fully bleached sulphate pulps.

Sample

The reference sample consisted of 29 fully bleached pulp sheets that were removed following the drying machine at a chemical sulphate pulp plant. The sample material was divided up so that 16 samples were used to form a calibration set, while the remaining 13 samples were used to form an off-line test set. Measurements using NIR spectroscopy, measurements with a fibre analyser and traditional assessments of pulp properties were carried out on all samples.

NIR Measurements

Figure 4:
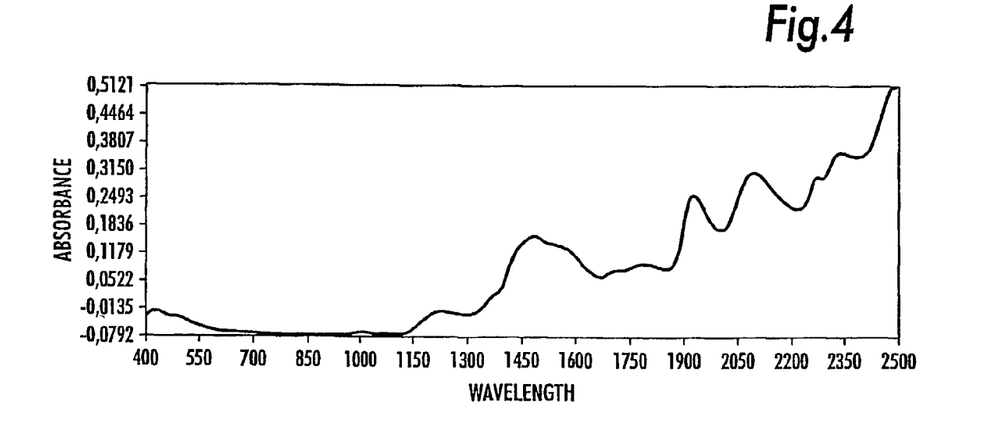
FIG. 4 shows an example of a measured NIR spectrum that is used in the invention.

NIR measurements were carried out using an NIRSystems 6500 instrument that is equipped with a transport module and a test cell with a surface of approx. 60 cm$^2$. The measurements were performed with reflectance directly on the unbeaten dry pulp sheets. The measuring range was 400–2500 nm with a resolution of 2 nm and each spectrum was a mean value of 32 sweeps. When using the entire measuring range, 1050 data points are obtained per sample. In the present example, the range between 1200–2500 nm was used, which generates 650 data points per sample. An NIR spectrum for a pulp sample is shown in FIG. 4.

Fibre Measurements

Figure 5A:
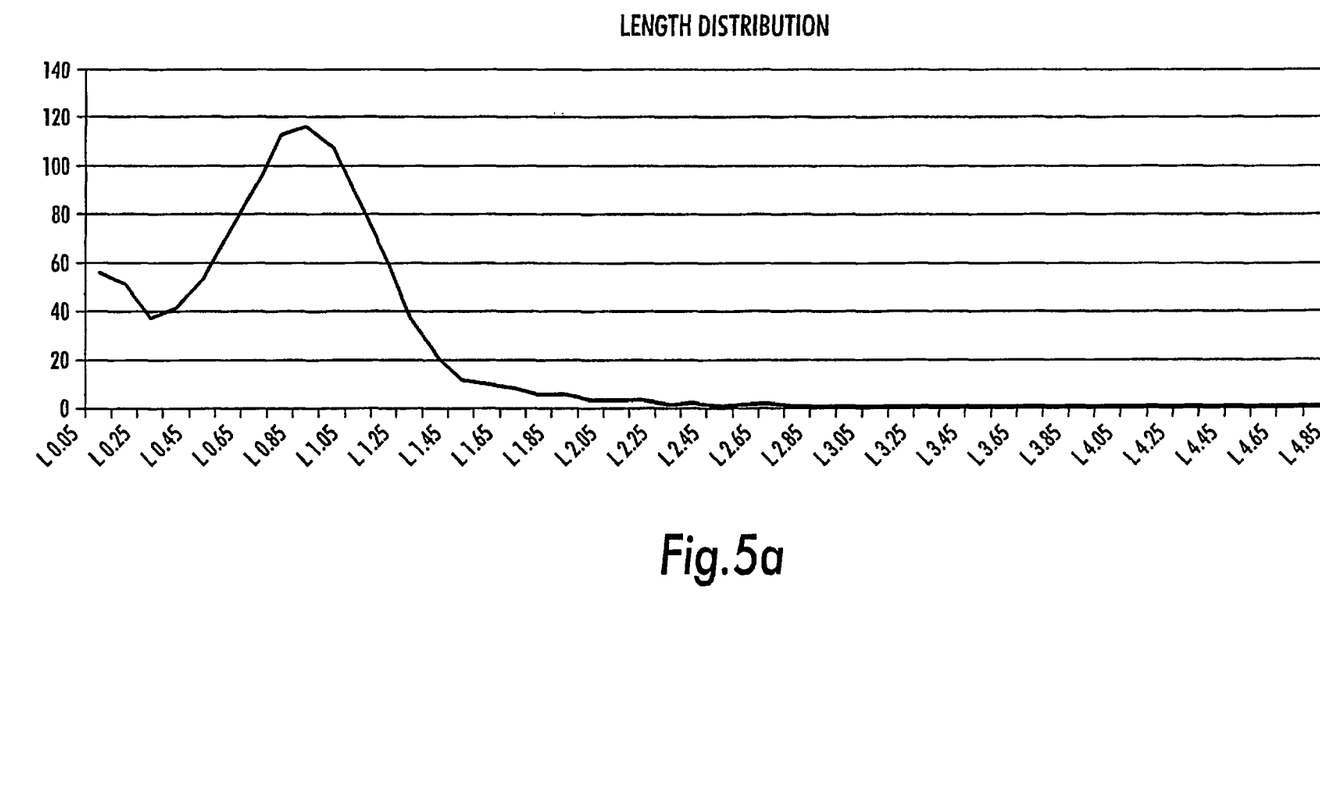
FIGS. 5a–c show an example of measured fibre property distributions that are used in the invention.
Figure 5B:
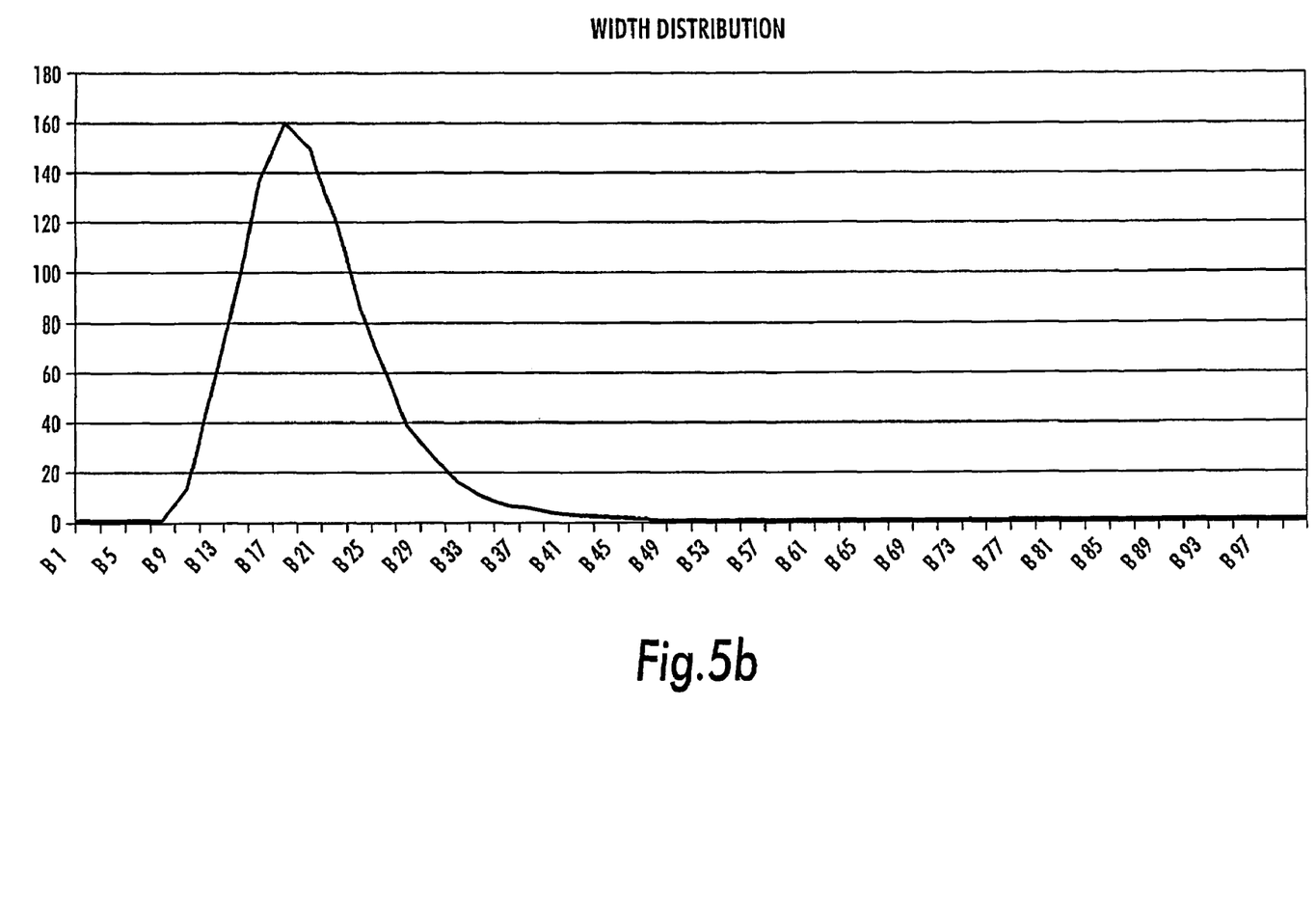
Figure 5C:
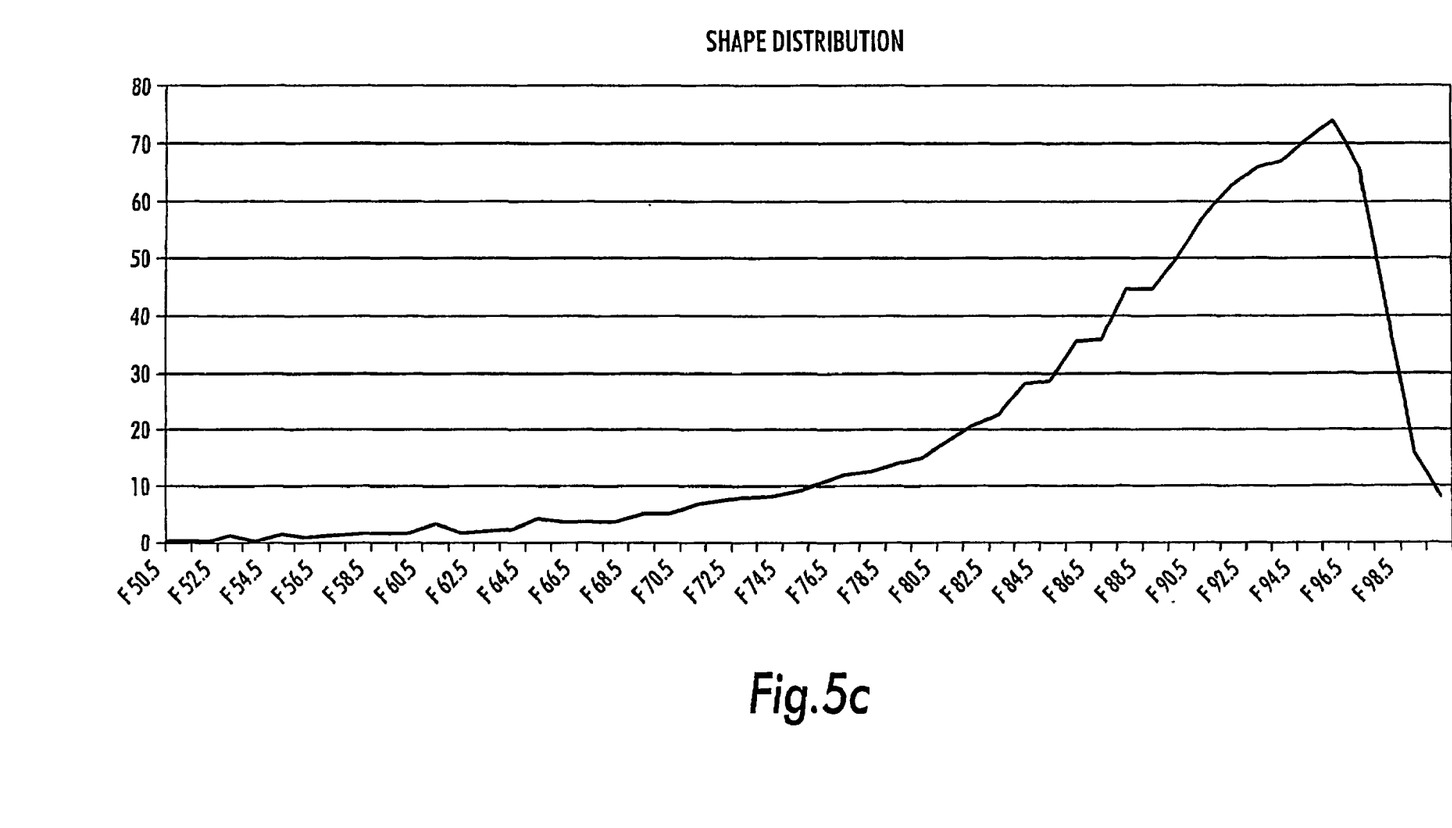

The fibre measurements were performed on a 0.05% pulp suspension of the unbeaten samples by means of the STFI FiberMaster. The instrument measures the fibre length, width, shape, flexibility and fibre weight per metre on 10000 fibres by using CCD cameras and image analysis, and supplies data in the form of distribution curves and mean values which together provide over 170 data points. The distribution curves for fibre length, width, and shape are shown in FIGS. 5a–c.

Determining the Sheet Properties

Assessments of the quality of the pulp samples were performed according to standardized methods on laboratory sheets produced from pulp beaten at different speeds using a PFI beater. At each speed, the dewatering resistance, density, tensile index, tear index, tensile rigidity index and air permeance were measured amongst other things. The beating requirement to achieve a certain attribute level was determined by interpolations.

The present example shows the results for prediction of the tensile index measured at 1000 PFI revolutions and the beating requirement to achieve a tensile index of 70 Nm/g. The tensile index is an important strength parameter and is defined as the force required to achieve a break in a paper strip that is clamped in a tensile tester.

The spectral data matrix from the NIR measurements was transformed in the example to another derivative to compensate for baseline drift Linearization of spectral data can also take place using Multiplicative Scatter Correction (MSC), Orthogonal Signal Correction (OSC) or Standard Normal Variate transformation (SNV).

Calibration models based on just NIR data, just fibre data and combinations of these were created by means of PLS in the software SIMCA P from UMETRICS. 650 data points were used from each NIR spectrum and 160 data points per sample were used from the FiberMaster measurements. The number of significant components was determined by cross-validation. The calibration model was tested using the off-line test set.

Figure 6A:
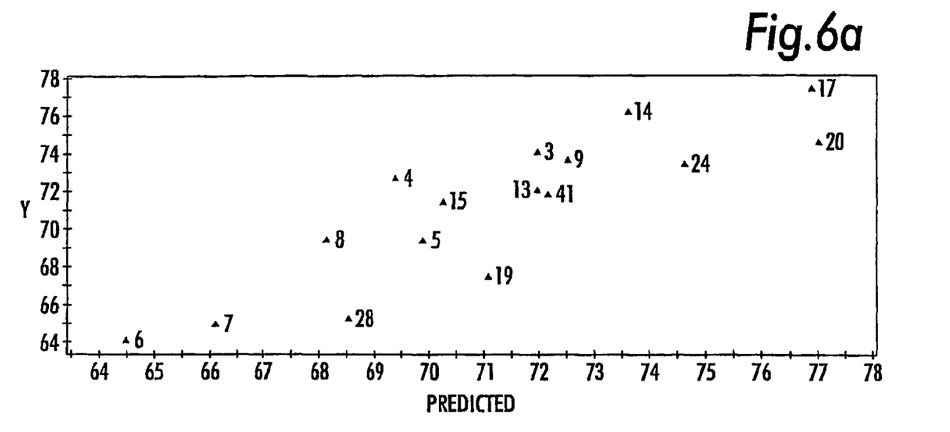
FIGS. 6a–c show calibration models for determining the tensile index measured at 1000 PFI revolutions, starting out from NIR data, fibre data or a combination thereof.
Figure 6B:
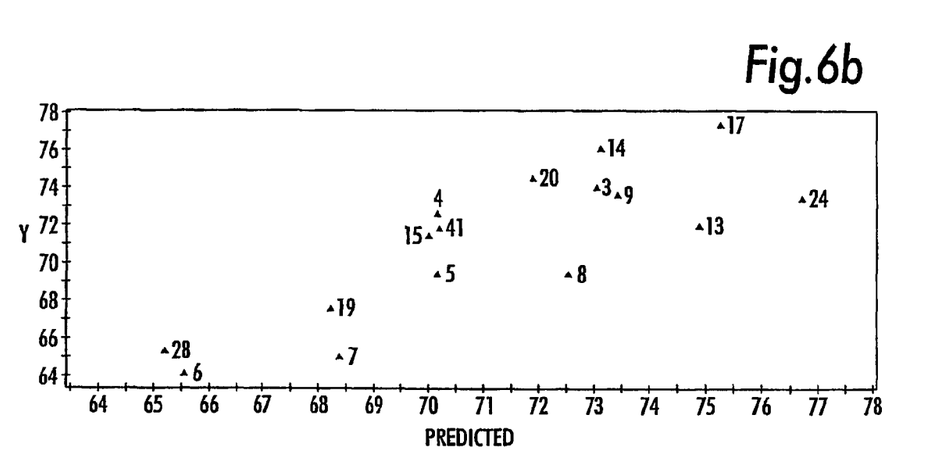
Figure 6C:
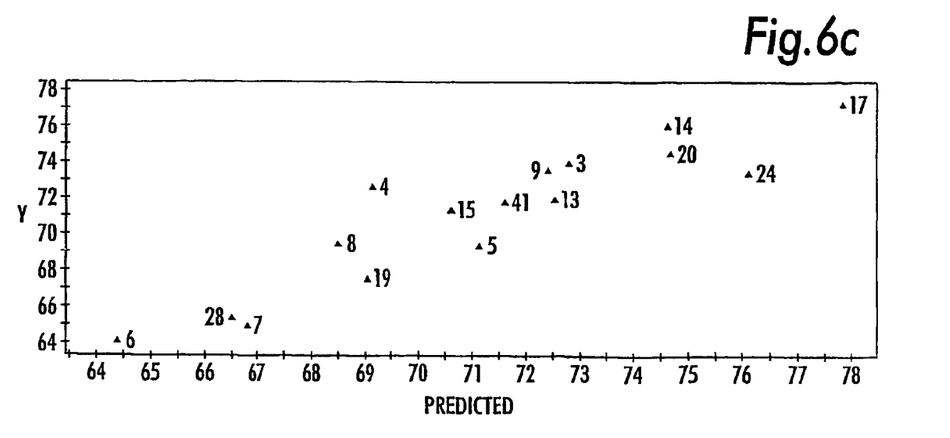
Figure 7A:
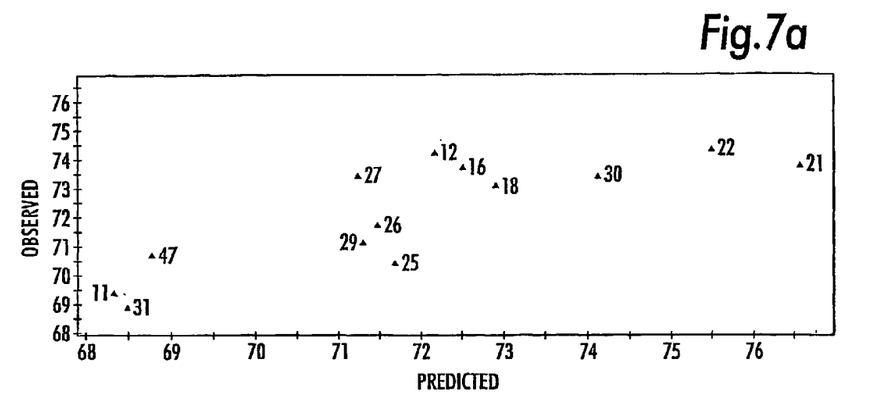
FIGS. 7a–c show the results of prediction from the calibration models in FIGS. 6a–c, FIGS. 8a–c show calibration models for determining the beating requirement to achieve the desired tensile index, starting out from NIR data, fibre data or a combination thereof.
Figure 7B:
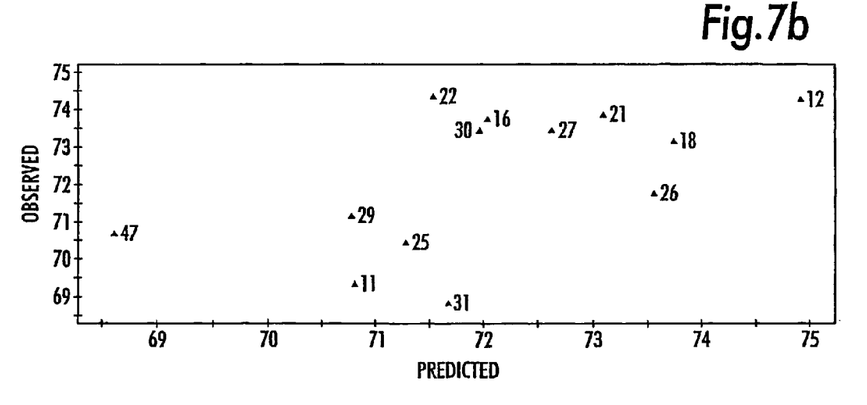
Figure 7C:
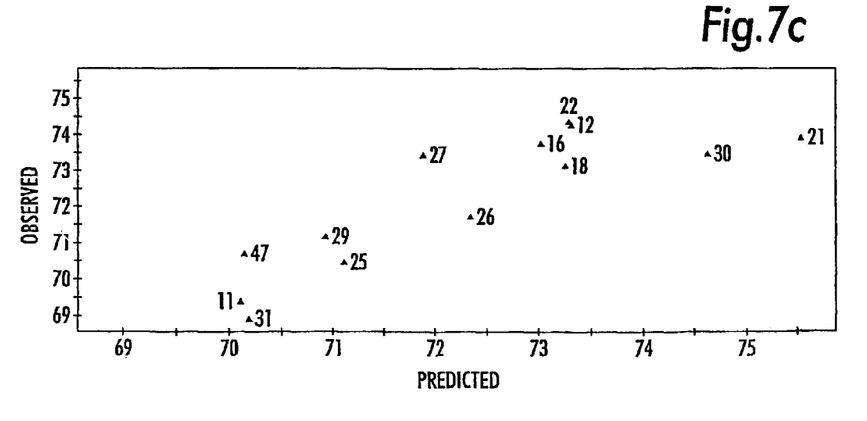
Figure 8A:
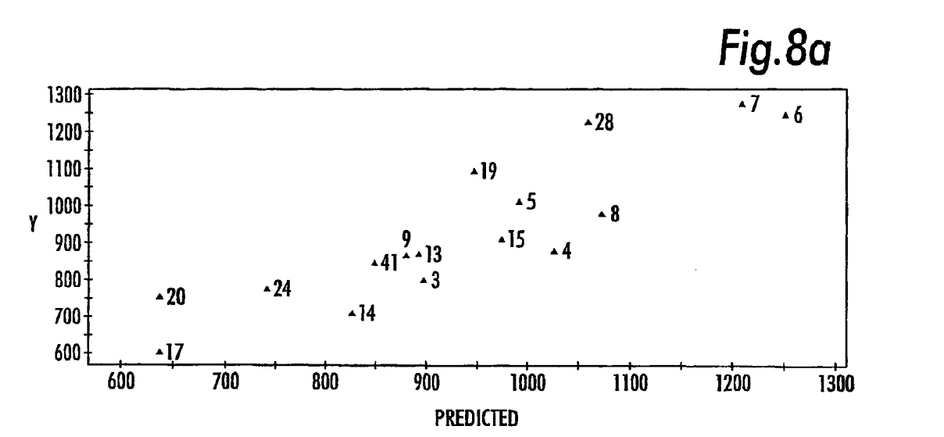
Figure 8B:
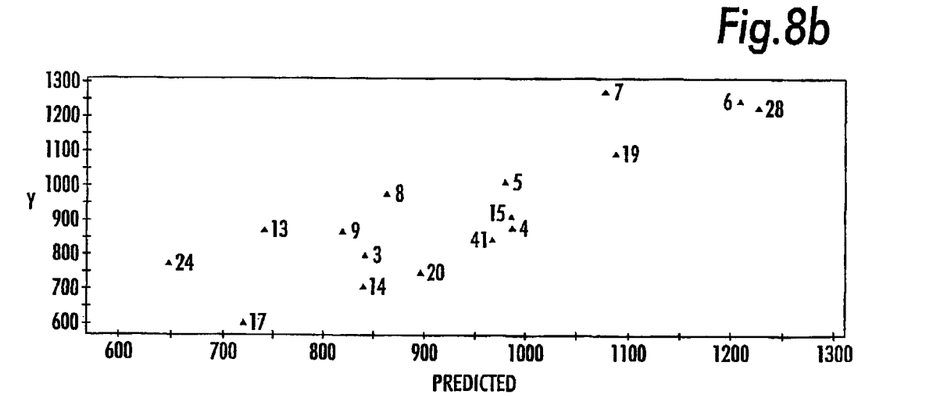
Figure 8C:
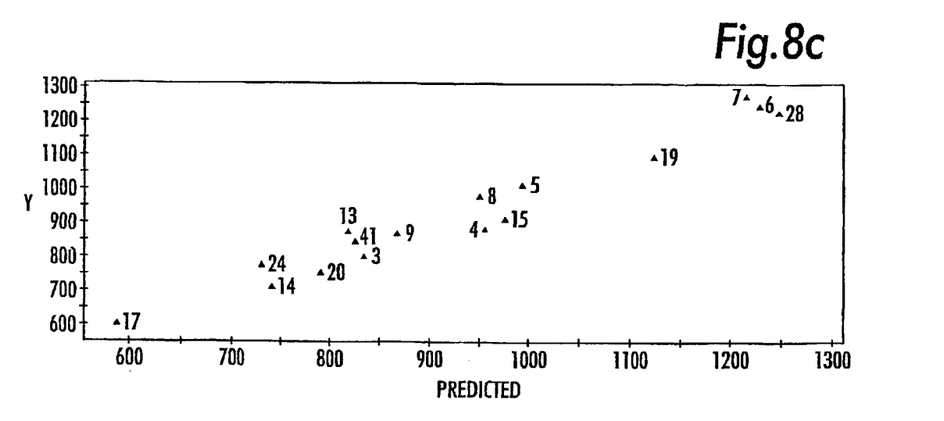
Figure 9A:
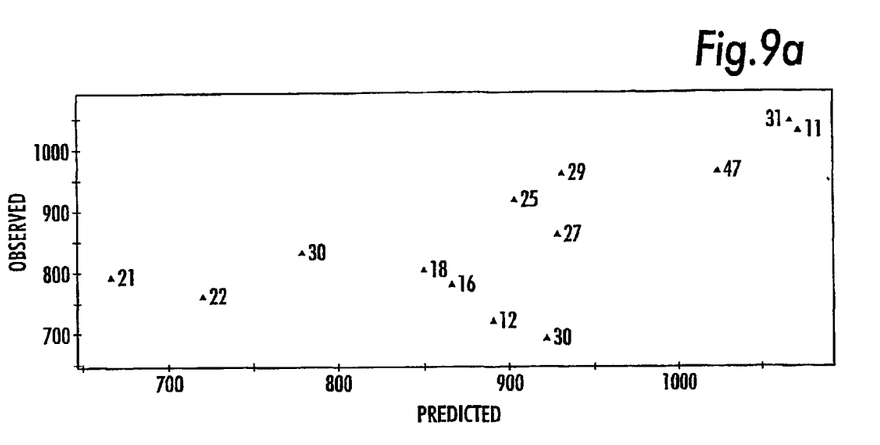
FIGS. 9a–c show the prediction results from the calibration models in FIGS. 8a–c.
Figure 9B:
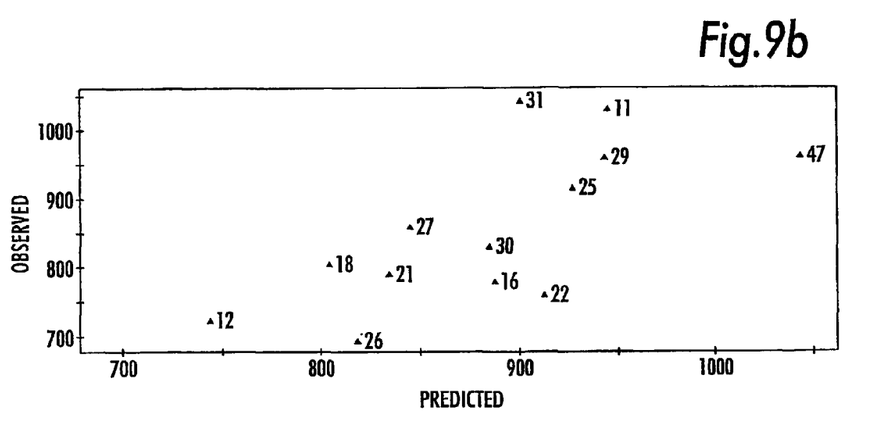
Figure 9C:
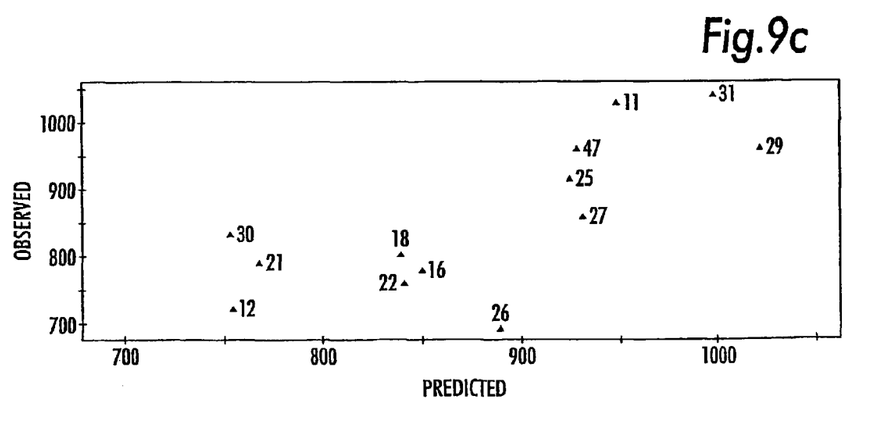

FIGS. 6a–c show the calibration model for determining the tensile index measured at 1000 PFI revolutions. In the figure, the analysed values for the tensile index are plotted against the predicted values. FIG. 6a is based on purely NIR data, FIG. 6b is based on purely FiberMaster data and FIG. 6c is based on the combination of these. FIGS. 7a–c show the prediction results for the off-line test set for the respective calibration model according to FIGS. 6a–c.

The models are summarised in Table 1. Both the calibration models and the prediction results were improved when using a combination of NIR and fibre analysis. Both R2Y, explained variance, and Q2, predicted variance, which must both be close to 1, increase. The model error, RMSEE (root mean squared error of estimation) and the prediction error RMSEP (root mean squared error of prediction) decrease.

TABLE 1

Model results for determining the tensile index at 1000 PFI revolutions

|  | Comp | R2Y | Q2 | RMSEE | RMSEP |
|---|---|---|---|---|---|
| NIR | 2 | 0.76 | 0.33 | 2.11 | 1.43 |
| FiberMaster | 1 | 0.69 | 0.50 | 2.32 | 1.61 |
| NIR + FiberMaster | 2 | 0.85 | 0.56 | 1.69 | 0.98 |

The beating requirement to obtain a desired value of the tensile index was modelled in the same way. FIGS. 8a–c and FIGS. 9a–c show calibration models and the results for the off-line test set. The models for the beating requirement are summarised in Table 2. The combination of NIR and FiberMaster produced an improvement in the model results here also.

TABLE 2

Model results for determining the beating
requirement for the tensile index 70 Nm/g

|  | Comp | R2Y | Q2 | RMSEE | RMSEP |
|---|---|---|---|---|---|
| NIR | 2 | 0.79 | 0.41 | 98 | 96 |
| FiberMaster | 1 | 0.70 | 0.54 | 112 | 82 |
| NIR + FiberMaster | 2 | 0.96 | 0.68 | 45 | 75 |

The invention is not restricted to the embodiments shown above, but can be varied within the scope of the following claims. It is perceived, for example, that the combination of NIR, fibre analysis and MVA can be carried out also on samples that are extracted at other positions in the pulp line, e.g. if the aim is primarily to control the pulp production process. The results of the analyses can also be utilized for feedback adjustment of the pulp production process. The invention can, in a broad aspect, also be used in the line for paper or paperboard manufacture, it being possible for example for the measuring position to be after beating or at beaters for different layers in a paperboard, with the possibility for example of determining a suitable waste proportion. It is also perceived that other equipment can be used, for example another fibre meter that can provide the fibre property distributions, and that several computers can be used and linked together for the different analyses and prediction.

The invention claimed is:

1. Method for predicting properties of a product that consists of cellulose-fibre-based pulp, paper or paperboard, wherein a suspension of cellulose fibre is subjected to analysis during manufacture of the product by spectroscopic measurements of a sample quantity of said suspension in a selected spectrum in the wavelength range 200–25000 nm, said method comprising:
    diluting each sample quantity prior to said analysis;
    dewatering and drying a first partial flow;
    subjecting said first partial flow to spectroscopic measurements in a selected spectrum in the wavelength range 200–25000 nm;
    analyzing a second partial flow of the diluted sample quantity for physical fibre data, by means of image analysis;
    each sample quantity analysed generating at least 100 data points from the spectroscopic measurements distributed in said selected spectrum, and at least 50 data points with regard to said physical fibre data, in the form of one or more physical fibre property distributions with regard to at least one physical property in the group consisting of fibre length, fibre width and fibre shape, which total of at least 150 data points are combined in multivariate data processing, for prediction of physical properties of said product, on the basis of calibrations previously executed that were carried out on samples with known physical properties.

2. Method according to claim 1, wherein said sample quantity of said suspension is extracted for analysis at-line or on-line in a process line for said manufacture of the product at least once every two hours.

3. Method according to claim 2, wherein said sample quantity suspension is extracted at least once per hour.

4. Method according to claim 2, wherein said sample quantity suspension is extracted at least four times per hour.

5. Method according to claim 2, wherein said sample quantity is extracted in a process line for pulp production.

6. Method according to claim 5, wherein said calibrations comprise calibrations against pulp samples that have been beaten with a number of different energy inputs, said prediction giving a measure of the product attributes that it is possible to achieve with one or more given energy inputs.

7. Method according to claim 5, wherein said sample quantity is extracted prior to beating of the pulp.

8. Method according to claim 5, wherein said sample quantity is extracted prior to beating of the pulp and directly prior to a drying stage for the pulp, which drying stage is directly prior to sale of dried pulp or directly prior to said beating of pulp.

9. Method according to claim 2, wherein said sample quantity is extracted at a position in a process line for paper or paperboard production.

10. Method according to claim 1, wherein the product properties predicted for an individual base paper bale or roll produced in pulp manufacture are compared with desired properties of said base paper bale or roll produced in pulp manufacture.

11. Method according to claim 1, wherein said spectrum consists of the wavelength range 400–2500 nm, in which spectrum at least 100 data points are generated for each sample quantity, which data points consist of mean values of at least 10 sweeps in the spectrum.

12. Method according to claim 11, wherein said spectrum consists of the wavelength range 780–2500 nm and at least 300 data points are generated for each sample quantity.

13. Method according to claim 12, wherein at least 800 data points are generated for each sample quantity.

14. Method according to claim 11, wherein the number of sweeps is 10.

15. Method according to claim 1, wherein said physical fibre data are obtained by means of a CCD camera, at least 50 data points being generated for each sample quantity, which data points consist of distribution data with regard to at least two physical attributes in the group consisting of fibre length, fibre width and fibre shape.

16. Method according to claim 15, wherein at least 150 data points are generated for each sample quantity.

17. Method according to claim 15, wherein said data points consist of distribution data with regard to all physical attributes in the group consisting of fibre length, fibre width, fibre shape, fibre weight per meter and fibre flexibility.

18. Method according to claim 1, wherein said dilution is carried out during agitation to a concentration of less than 0.5%, and said dewatering and drying is carried out to at least 50% dry content.

19. Method according to claim 18, wherein said dilution is carried out during agitation to a concentration of less than 0.1%, and said dewatering and drying is carried out to at least 70% dry content.

20. Method according to claim 18, wherein said dewatering and drying is carried out by filtering combined with forced air drying.

21. Method according to claim 20, wherein said forced air drying is by direct contact with compressed air.

* * * * *